United States Patent [19]
Cinberg et al.

[11] Patent Number: 5,254,120
[45] Date of Patent: Oct. 19, 1993

[54] MYRINGOTOMY VENTILLIATION TUBE, METHOD, APPLICATOR AND KIT

[76] Inventors: James Z. Cinberg, 167 N. Ridgewood Rd., South Orange, N.J. 07079; Peter J. Wilk, 185 W. End Ave., New York, N.Y. 10023

[21] Appl. No.: 959,672

[22] Filed: Oct. 13, 1992

Related U.S. Application Data

[63] Continuation-in-part of Ser. No. 833,511, Feb. 11, 1992, Pat. No. 5,178,623, and a continuation-in-part of Ser. No. 921,308, Jul. 28, 1992, Pat. No. 5,207,685.

[51] Int. Cl.⁵ .............................................. A61F 17/00
[52] U.S. Cl. .................................... 606/109; 606/108; 606/167; 606/170
[58] Field of Search .................. 606/1, 108, 109, 167, 606/170, 180; 623/10; 604/164, 264; 128/9

[56] References Cited

U.S. PATENT DOCUMENTS

| | | |
|---|---|---|
| 3,530,860 | 9/1970 | Majoros . |
| 3,871,380 | 3/1975 | Heros . |
| 3,888,258 | 6/1975 | Akiyama . |
| 3,897,786 | 8/1975 | Gearnett et al. ............ 606/108 |
| 3,948,271 | 4/1976 | Akiyama . |
| 3,982,545 | 9/1976 | Silverstein . |
| 4,168,697 | 9/1979 | Cantekin . |
| 4,764,168 | 8/1988 | Suh . |
| 4,775,370 | 10/1988 | Berry . |
| 4,971,076 | 11/1990 | Densert et al. . |
| 5,026,378 | 6/1991 | Goldsmith . |
| 5,047,053 | 9/1991 | Jahn . |
| 5,053,040 | 10/1991 | Goldsmith . |

Primary Examiner—Stephen C. Pellegrino
Assistant Examiner—Glenn Dawson
Attorney, Agent, or Firm—R. Neil Sudol; Henry D. Coleman

[57] ABSTRACT

A tympanic ventilation tube device for releasing fluid from the middle ear includes a tubular member, a first flange connected to a proximal end of the tubular member, a second flange connected to a distal end of the tubular member, and a cutting element connected to either the tubular member or the second flange. The cutting element projects in a generally distal direction and serves to facilitate the incising of the tympanic membrane during the insertion of the tubular member, wherein the first flange and the second flange seat against opposite sides of the membrane following the insertion. A spring-loaded protector is movably mounted to either the tubular member or the second flange for retracting in a proximal direction to expose the cutting element during an incising of a tympanic membrane by the cutting element in an insertion operation and for extending in a distal direction to cover the cutting element upon insertion of the cutting element and the distal flange through the tympanic membrane. A kit for insertion of the tube includes a placement obturator, a disposable otoscope, a syringe, a culture vial, a local anesthetic applicator and a kit container.

4 Claims, 6 Drawing Sheets

MYRINGOTOMY VENTILLIATION TUBE, METHOD, APPLICATOR AND KIT

CROSS-REFERENCE TO RELATED APPLICATION

This application is a continuation-in-part of application Ser. No. 833,511 filed Feb. 11, 1992, now U.S. Pat. No. 5,178,623 and application Ser. No. 921,308 filed Jul. 28, 1992, now U.S. Pat. No. 5,207,685.

FIELD OF THE INVENTION

This invention relates to a ventilation tube which is placed in a patient's tympanic membrane for purposes of pressure equalization between the middle ear cleft and the ambient atmospheric pressure and also for draining fluid from the middle ear. In addition, this invention relates to a surgical technique for use in obtaining a sample of middle ear fluid from the middle ear cleft during a myringotomy operation. Also, this invention relates to an otoscope for use in performing a myringotomy. This invention further relates to a kit for use in performing a myringotomy.

BACKGROUND OF THE INVENTION

Children frequently have an abnormal condition characterized by fluid in the middle ear cleft. A myringotomy or tympanostomy with placement of a ventilation or pressure equalization tube is a surgical operation performed on the ear drum to drain the fluid and ventilate the middle ear for a longer period than would be possible with only an incision of the ear drum as spontaneous drum closure occurs in a week or two after the incision of the ear drum: a result of standard repair processes of an incised ear drum. During a myringotomy and tube placement, as conventionally performed, an ear knife cuts the ear drum and creates an incision. Complications of this procedure are inadvertant laceration of the external ear canal as the knife moves towards or away from the drum and creation of a drum incision which is either too short or too long. Then a ventilation tube is inserted through the incision and manipulated to remain seated in the incision, thereby providing a duct or channel for draining fluid from the middle ear and ventilating the middle ear space via the external auditory canal.

During insertion down into the external auditory canal and placement in the tympanic membrane, the ventilation tube is held by a special grasping forceps. Because the ventilation tube is so tiny and the ear drum so delicate, a myringotomy and tube placement is an especially sensitive operation and gives rise to considerable challenges to a surgeon's dexterity and patience.

OBJECTS OF THE INVENTION

An object of the present invention is to provide an improved ventilation or pressure equalization tube for use in ventilating and/or draining fluid from the middle ear.

A related object of the present invention is to provide an improved method for performing a myringotomy.

Another, more particular, object of the present invention is to provide a myringotomy method which is easier, quicker and more economical than conventional procedures.

A further particular object of the present invention is to provide such a method which facilitates the collection of fluid sample from a patient's middle ear cleft.

An even more particular object of the present invention is to provide an implant that can both incise the ear drum and serve as a pressure equalization device.

These and other objects of the present invention will be apparent from the descriptions and illustrations herein.

SUMMARY OF THE INVENTION

A tympanic ventilation tube device for releasing fluid from the middle ear comprises, in accordance with the present invention, a tubular member, a first flange connected to a proximal end of the tubular member, a second flange connected to a distal end of the tubular member, and a cutting element connected to either the tubular member or the second flange. The cutting element projects in a generally distal direction and serves to facilitate the incising of the tympanic membrane during the insertion of the tubular member, wherein the first flange and the second flange seat against opposite sides of the membrane following the insertion. A spring-loaded protector is movably mounted to either the tubular member or the second flange for retracting in a proximal direction to expose the cutting element during an incising of a tympanic membrane by the cutting element in an insertion operation and for extending in a distal direction to cover the cutting element upon insertion of the cutting element and the distal flange through the tympanic membrane.

According to another feature of the present invention, the cutting element includes a plurality of angularly spaced radially oriented arms each formed on a distal side with a cutting edge. Preferably, the arms are connected to the second flange. The arms may be rectangular or triangular.

According to a further feature of the present invention, the protector includes a collar element which circumferentially surrounds the cutting element in an extended configuration of the protector.

According to another feature of the present invention, the device further comprises a tubular obturator releasably connected to the tubular member at a proximal end thereof. The obturator communicates with the tubular member, whereby a fluid sample may be drawn into the obturator upon an insertion of the cutting element through the tympanic membrane.

A tympanic ventilation tube device for releasing fluid from the middle ear comprises, in accordance with another embodiment of the present invention, a tubular member, a first flange connected to a proximal end of the tubular member, a second flange connected to a distal end of the tubular member, and a cutting element connected to a given one of the tubular member and the second flange. The cutting element projects in a generally distal direction and includes a plurality of angularly spaced radially oriented arms each formed on a distal side with a cutting edge. The cutting element facilitates the incising of the tympanic membrane during the insertion of the tubular member, wherein the first flange and the second flange seat against opposite sides of the membrane following the insertion.

Preferably, the arms are connected to the second flange and are rectangular or triangular.

A method for ventilating and/or releasing fluid from the middle ear in accordance with the present invention uses a tympanic ventilation tube having a first flange at one end, a second flange at an opposite end, and a cutting edge projecting from one of the tubular member and the second flange, the tube being releasably attached to a distal end of a hollow obturator. The method comprises the step of manipulating the obturator to press the cutting edge against a tympanic membrane so as to form a perforation in the membrane and to introduce the second flange through the perforation so that the first flange and the second flange seat against opposite sides of the membrane following such introduction. Subsequently, fluid is aspirated from the middle ear cleft through the tube and into at least a distal end portion of the obturator. The obturator is removed from the tube while leaving the tube seated in the tympanic membrane.

An otoscope for use in performing a myringotomy comprises, in accordance with the present invention, a conical nose portion and a cover member attached to the nose portion at a wider end thereof. The cover member is provided with a magnifying lens and an opening for enabling the insertion of an instrument through the cover member and the nose portion into a patient's ear canal. A handle is attached to the nose portion at the wider end, the handle being provided with a light source. A prism, optical fiber or other optical element is provided transmitting light from the source to the nose portion and for directing light in a direction generally coaxial with the nose portion.

Pursuant to another feature of the present invention, the handle is removably attached to the nose portion. The nose portion and the cover member may be formed as an integral piece.

A tympanic ventilation tube device for releasing fluid from the middle ear comprises, in accordance with yet another embodiment of the present invention, a tubular member, a first flange connected to one end of the tubular member, a second flange connected to an opposite end of the tubular member, and a cutting element attached to the second flange. The cutting element is a hollow screw-type extension projecting in the distal direction from the distal flange.

In accordance with further features of this embodiment of the present invention, the cutting element has an opening at a distal end, spaced from the second flange, the opening communicating with the tubular member and being disposed in a plane angled with respect to a longitudinal axis of the tubular member. A substantially circular cutting edge surrounds and defines the opening.

A kit for use in performing a myringotomy operation, comprises, in accordance with the present invention, a ventilation tube provided at a distal end with a cutting edge, a placement obturator releasably connected to the tube at a proximal end thereof, a disposable otoscope, a syringe connectable to a proximal end of the obturator for aspirating a quantity of fluid into a distal end of the obturator, a culture vial, a local anesthetic applicator having an elongate handle portion, and a container enclosing the ventilation tube, the placement obturator, the otoscope, the syringe, the vial, and the anesthetic applicator.

A myringotomy ventilation tube in accordance with the present invention represents a considerable advance. A myringotomy and tube placement can be performed more quickly, more safely and with greater ease, inasmuch as the incision and ventilation tube insertion steps are performed by the same instrumentation, namely, the ventilation tube itself.

This technique in accordance with the present invention results in considerable savings inasmuch as reusable or disposable ear drum knives are no longer needed. Such knives are resterilized and stored or thrown away, respectively, after a single operation. Although the ventilation tube in accordance with the invention will be more expensive than a conventional ventilation tube, it is expected that a cost saving will still accrue.

A method in accordance with the present invention facilitates the collection of a fluid sample from the middle ear cleft. The sample is collected in essentially the same procedure as the tube placement.

A myringotomy is further facilitated by a otoscope and a kit in accordance with the present invention.

DETAILED DESCRIPTION

Figures 1, 2, 3:
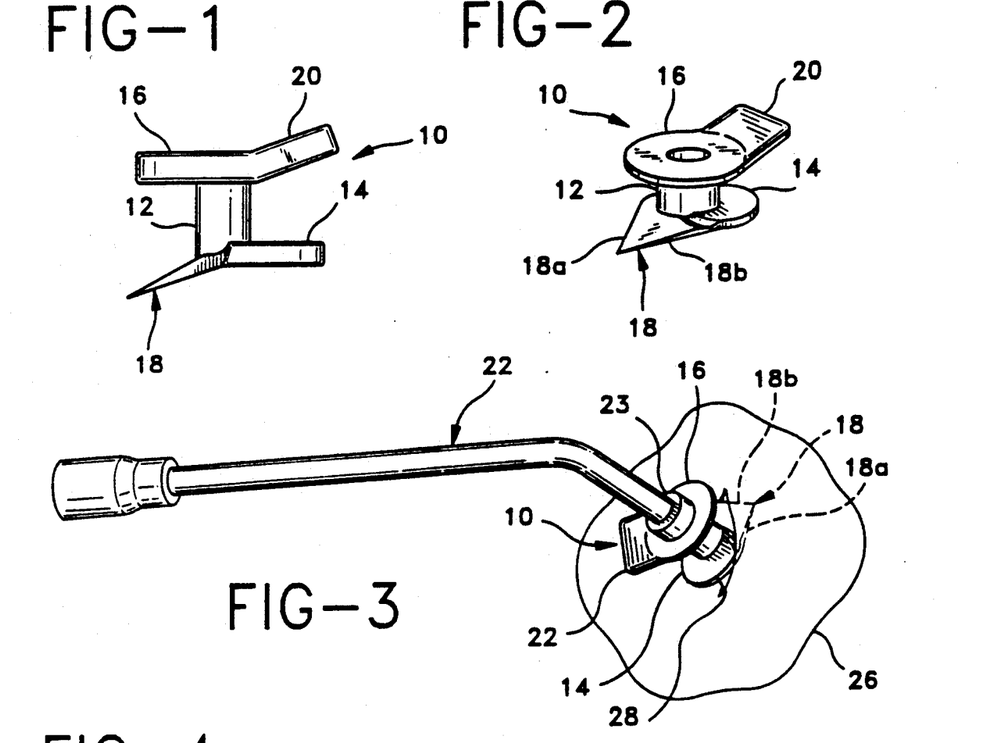
FIG. 1 is side elevational view, on a substantially enlarged scale, of an implant or ventilation tube for use in incising an ear drum in a myringotomy operation and for subsequently serving as a pressure equalization device.
FIG. 2 is a perspective view, on an enlarged scale, of the ventilation tube of FIG. 1.
FIG. 3 is a perspective view, also on an enlarged scale, of the ventilation tube of FIG. 1 connected to the distal end of an applicator rod.

As illustrated in FIGS. 1 and 2, a ventilation tube 10 for use in performing a myringotomy and subsequent pressure equalization comprises a tubular member 12, a first flange or collar 14 connected to a distal end of the tubular member, and a second flange or collar 16 connected to a proximal end of the tubular member. Distal flange 14 is provided along a distal side, i.e., on a side opposite proximal flange 16, with a cutting edge 18 comprising a pair of straight edge segments 18a and 18b oriented at an acute angle with respect to one another to form a cutting wedge extending in a direction away from proximal flange 16.

Ventilation tube 10 further comprises a non-cutting tongue or extension 20 connected to proximal flange 16. Tongue extension 20 projects at a shallow angle from proximal flange 16 on a side thereof opposite distal flange 14.

Figure 4:
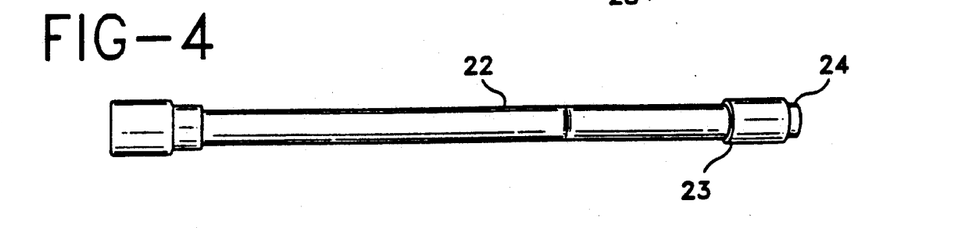
FIG. 4 is a side elevational view, on an enlarged scale, of the applicator rod of FIG. 3, showing a nose extension for releasably coupling the ventilation tube to the application rod.

As depicted in FIG. 3, an elongate applicator rod or obturator 22 is removably coupled to ventilation tube 10 prior to the commencement of a myringotomy. As illustrated in FIG. 4, applicator rod 22 is formed at a distal end with a collar 23 and a distally extending nose portion 24 for releasably holding ventilation tube 10. Nose portion 24 may be inserted into ventilation tube 10 in a loose friction fit.

Applicator rod 22 is made of a material such as a metal or alloy having a limited malleability. Thus, applicator rod 22 may be bent, as shown in FIG. 3, for example, to assume a different configuration prior to the insertion of the rod and ventilation tube 10 into the external auditory canal of a patient. The malleability of applicator rod 22 facilitates the disposition of ventilation tube 10 at an appropriate place in the patient's tympanic membrane.

Ventilation tube 10 can have different dimensions and still be effective for seating in a patient's tympanic membrane. In one configuration, flanges 14 and 16 are approximately three millimeters in diameter, while tubular member 12 has an inner diameter of approximately 1.25 millimeters. Flanges 14 and 16 are spaced from one another by a distance approximately equal to the thickness of a tympanic membrane, for example, approximately 1.55 millimeters.

It is to be noted that applicator rod 22 may be used with conventional ventilation tubes, for example, tubes with flanges or collars, but without cutting edge 18 or tongue extension 20. In such a case, the incision in the patient's tympanic membrane is formed conventionally, with a knife prior to the insertion of the ventilation tube.

In using tympanic ventilation tube 10 and applicator rod 22, ventilation tube 10 is first mounted to the distal end of applicator rod 22. Applicator rod 22 is then manipulated to insert ventilation tube 10 through the patient's auditory canal and to pres cutting edge 18 against the tympanic membrane 26 (FIG. 3) so as to form a perforation or incision 28 (FIG. 3) therein. Preferably, upon achieving contact between ventilation tube 10 and the tympanic membrane, applicator rod 22 and concomitantly ventilation tube 10 are pressed towards the drum to facilitate the penetration of the tympanic membrane by cutting edge 18.

Upon penetration of cutting edge 18 through the tympanic membrane 26 to form perforation 28, applicator rod 22 is manipulated to insert distal flange 14 through the perforation, while maintaining proximal flange 16 on the outside of the tympanic membrane. Upon the seating of ventilation tube 10 so that distal flange 14 and proximal flange 16 are disposed on opposite sides of the tympanic membrane, nose portion 24 of applicator rod 22 is removed from ventilation tube 10.

Figure 5:
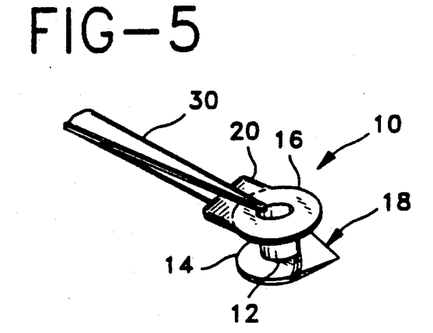
FIG. 5 is a perspective view, on an enlarged scale, of the ventilation tube of FIGS. 1-3, showing a grasping forceps holding the ventilation tube.
Figure 6:
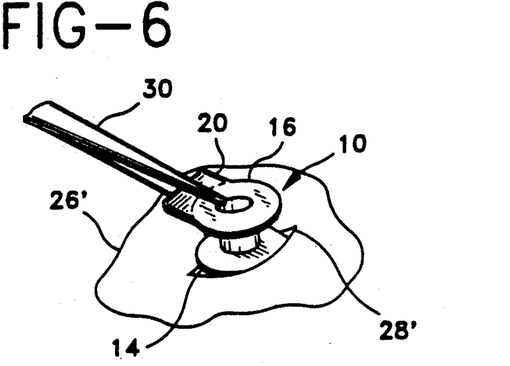
FIG. 6 is a perspective view, on an enlarged scale, of the ventilation tube and grasping forceps of FIG. 5, showing placement or removal of the ventilation tube from an incision formed in an ear drum.

It is to be noted that ventilation tube 10 may be inserted with instrumentation other than applicator rod 22. For example, as depicted in FIGS. 5 and 6, a grasping forceps 30 may be used to press ventilation tube 10 against tympanic membrane 26', to incise perforation 28,, to insert distal flange 14 through the perforation or incision, and to seat ventilation tube 10 in the incision. Alternatively, another instrument (not illustrated) which may be used to perform these steps has an inner tube with a distal end insertable into tubular member 12 and further has an outer tube coaxially surrounding the inner tube and slidable in a distal direction with respect thereto to eject ventilation tube 10 from the distal end of the inner tube upon seating of the ventilation tube in the ear drum.

Figure 7:
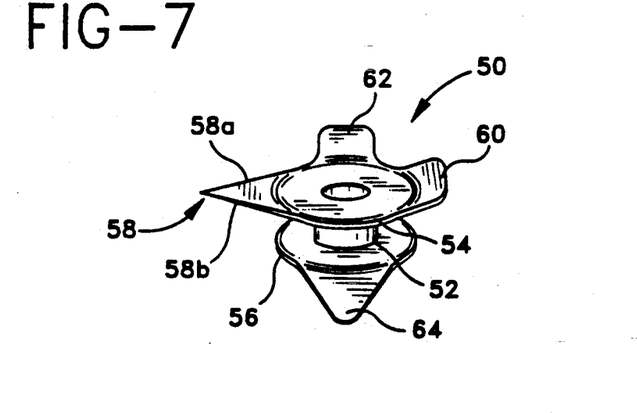
FIG. 7 is a schematic perspective view of another tympanic ventilation or pressure equalization tube with an integral incising edge.

As illustrated in FIG. 7, another tympanic ventilation or pressure equalization tube 50 for ventilating and/or releasing fluid from the middle ear comprises a tubular member 52 provided with a first or proximal flange 54 and a second or distal flange 56 connected to opposite ends of tubular member 52. Proximal flange 54 is provided with a cutting edge 58 comprising a pair of straight edge segments 58a and 58b oriented at an acute angle with respect to one another to form a cutting wedge extending in a lateral or transverse direction away from proximal flange 54.

Figure 8A:
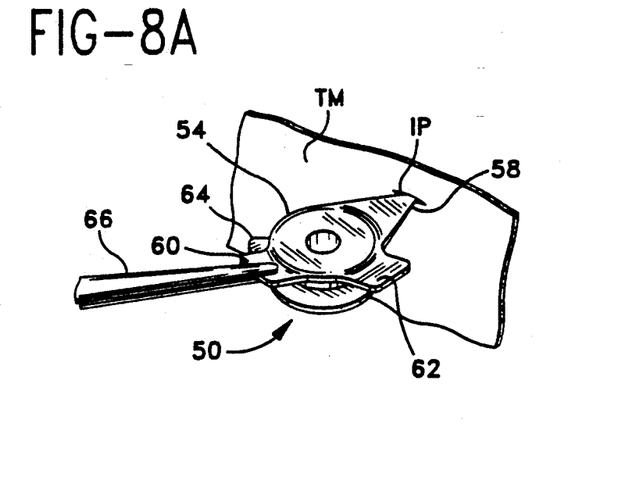
FIGS. 8A-8E are schematic perspective views depicting successive steps in the use of the tympanic ventilation or pressure equalization tube of FIG. 7.
Figure 8B:
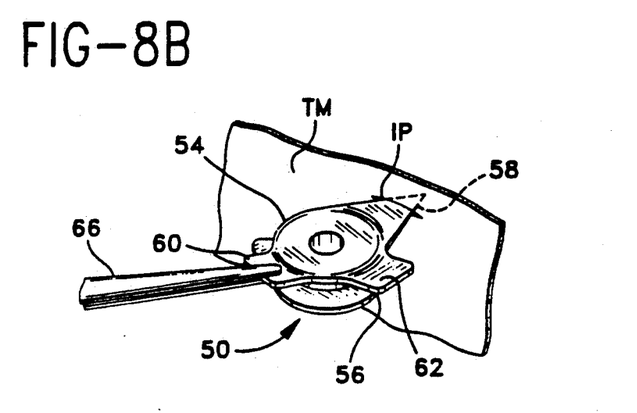
Figure 8C:
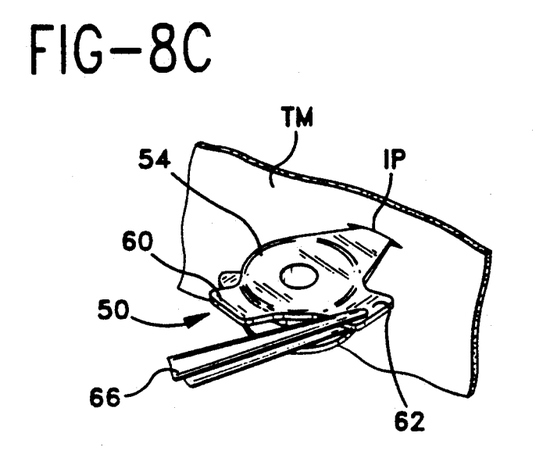
Figure 8D:
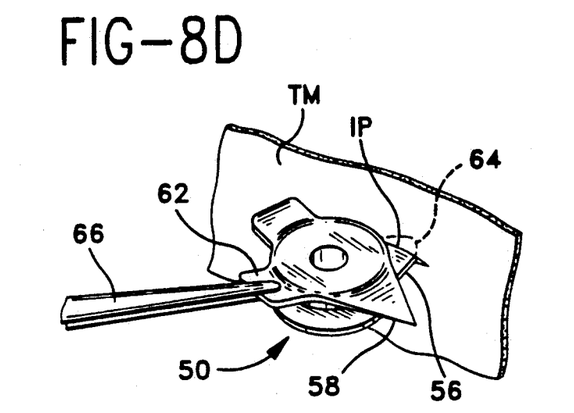
Figure 8E:
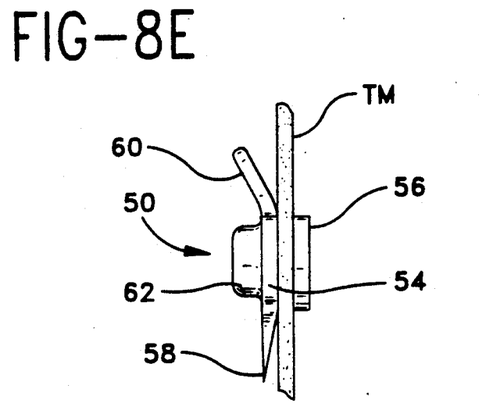

Proximal flange 54 is further provided with a first tongue extension 60 angularly spaced 180° from cutting edge 58 and a second tongue extension 62 angularly spaced 90° from cutting edge 58. Extension 60 facilitates grasping the device to apply pressure through cutting edge 58 to incise the tympanic membrane TM (FIGS. 8A-8E) during an insertion of tubular member 52, while proximal flange 54 and distal flange 56 seat against opposite sides of the membrane following the insertion, as illustrated in FIG. 8E.

Preferably, at least part of distal flange 56 is flexible for facilitating incising and insertion operations, described in detail hereinafter with reference to FIGS. 8A-8E. Flange 56 is also provided with a preferably rigid tongue extension 64 which facilitates insertion of distal flange 56 through an incision or perforation IP (FIGS. 8A-8E) formed in tympanic membrane TM.

In utilizing the tympanic ventilation or pressure equalization tube of FIG. 7 for ventilating and/or releasing fluid from the middle ear, cutting edge 58 is pressed against tympanic membrane TM so as to form incision IP in the membrane. To that end, a grasping forceps 66 is manipulated by the ear surgeon to clamp tongue extension 60 and to incise membrane TM, as illustrated in FIGS. 8A and 8B. FIG. 8B shows a later stage in the incising procedure, wherein distal flange 56 bends against tympanic membrane TM in response to the pressure exerted by the surgeon.

Upon formation of incision or perforation IP, tongue extension 60 is released, thereby temporarily leaving the ventilation tube held in membrane TM by cutting edge 58. Forceps 66 is then manipulated to grasp tongue extension 62, as illustrated in FIG. 8C, and to pull the ventilation tube in the proximal direction to remove cutting edge 58 from perforation IP. Ventilation tube 50 may then be rolled against tympanic membrane at that juncture to pivot the tube relative to forceps 66 so that forceps 66 grasp tongue extension 62 at the angle illustrated in FIG. 8D.

Alternatively, upon formation of incision or perforation IP, tongue extension 60 is used to pull cutting edge 58 from incision IP and to place ventilation tube 50 upon tympanic membrane TM. Forceps 66 is then manipulated to grasp tongue extension 62 at the angle illustrated in FIG. 8D.

Upon the removal of cutting edge 58 from incision IP and the grasping of tongue extension 62 at a suitable angle, forceps 66 is used to move tongue extension 64 of distal flange 56 through incision IP (FIG. 8D), while maintaining proximal flange 54 on an outer side of tympanic membrane TM to thereby dispose the tube in the membrane so that flanges 54 and 56 are seated against opposite sides of membrane TM, as illustrated in FIG. 8E. During the insertion of distal flange 56 through incision IP, that flange may distort slightly, owing to its inherent flexibility, to facilitate the insertion procedure.

The tympanic ventilation or pressure equalization tube of FIG. 7 and the associated method described above with reference to FIGS. 8A-8E serve to place the cutting edge 58 on the outer side of tympanic membrane TM, thereby reducing the chances of possible damage to organs of the middle ear.

Figure 9:
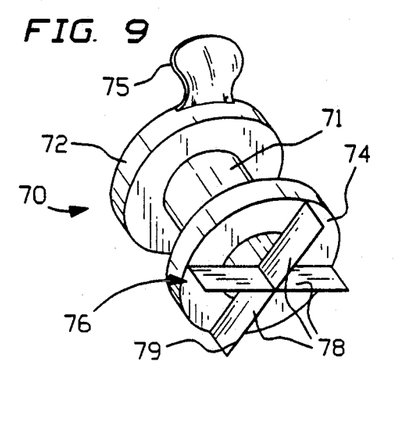
FIGS. 9-15 are schematic perspective views, on a substantially enlarged scale, of respective implant or ventilation tubes in accordance with the present invention for use in incising an ear drum in a myringotomy operation and for subsequently serving as pressure equalization devices.

As illustrated in FIG. 9, a tympanic ventilation tube device 70 for releasing fluid from the middle ear comprises a tubular member 71, a first annular flange 72 connected to a proximal end of the tubular member, a second annular flange 74 connected to a distal end of the tubular member, and a cutting element 76 connected to the second flange 74. A tongue extension 75 is attached to proximal flange 72. Cutting element 76 projects in a generally distal direction from flange 74 and includes four rectangular plates or arms 78 each formed on a distal side with a cutting edge 79. Arms 78 are angularly spaced from each other and radially oriented to form a cross-shaped configuration when viewed from an axial direction. Cutting element 76 facilitates the incising of a tympanic membrane during a disposition of tube device 70 in a myringotomy and tube placement procedure. Upon such placement of tube device 70, flanges 72 and 74 seat against opposite sides of the tympanic membrane. The angular spacing and configuration of arms 78 of cutting element 76 enables fluid from the middle ear to subsequently drain through tubular member 71.

Figure 10:
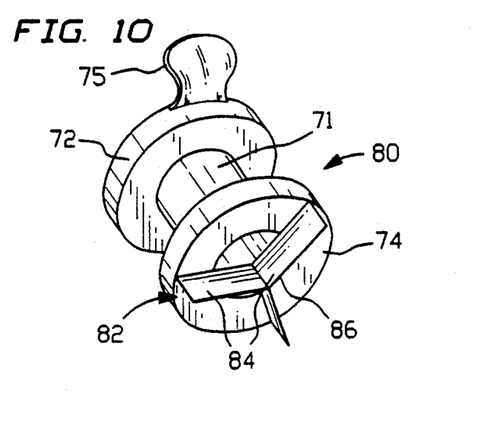

FIG. 10 depicts a tympanic ventilation tube device 80 similar to device 70 of FIG. 9. Like elements in the two figures are provided with the same reference designations. Tube 80 differs from tube 70 only in that tube 80 has a cutting element 82 with three, rather than four, rectangular plates or arms 84 which are angularly equispaced and provided with respective cutting edges 86 on a distal side.

Figure 11:
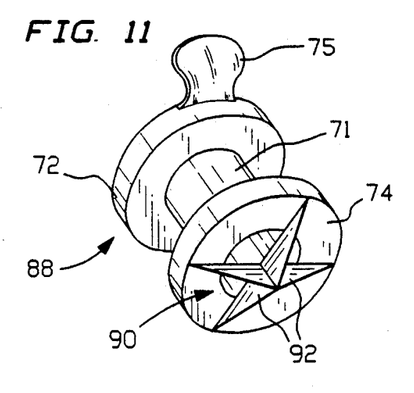

FIG. 11 shows a tympanic ventilation tube device 88 similar to device 70 of FIG. 9. The same elements in the two figures are provided with identical reference numerals. Tube 88 differs from tube 70 only in that tube 88 has a cutting element 90 formed with four triangular, rather than rectangular, plates or arms 92.

Figure 12:
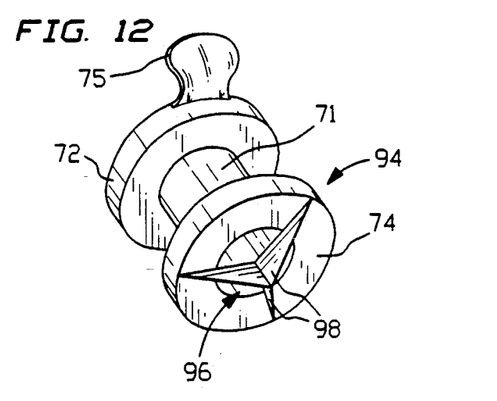

FIG. 12 illustrates a tympanic ventilation tube device 94 similar to device 80 of FIG. 10 and device 88 of FIG. 11. Like parts bear like reference designations. Tube 94 differs from tube 80 only in that tube 94 has a cutting element 96 formed with triangular, rather than rectangular, plates or arms 98. Tube 94 differs from tube 88 only in that cutting element 96 of tube 94 is formed with three, rather than four, triangular plates or arms 98.

Figure 13:
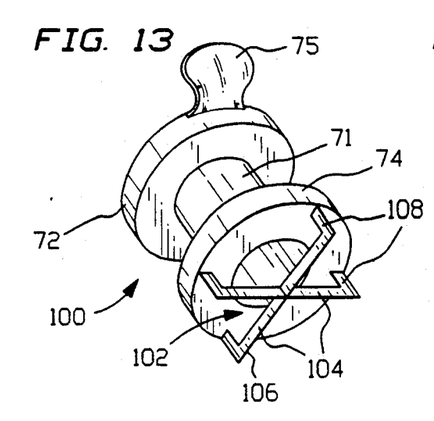

As depicted in FIG. 13, another tympanic ventilation tube device 100 has the same structure of tubular member 71, first annular flange 72 connected to the proximal end of the tubular member, and second annular flange 74 connected to the distal end of the tubular member. A cutting element 102 on distal flange 74 has four L-shaped plates or arms 104 connected to one another in a cross-shaped configuration. Cutting edges 106 on L-shaped arms 104 are pointed in a distal direction. Fingers 108 on arms 104 serve to space the body of cutting element 102 from flange 74 and facilitate the collection or drainage of middle ear fluid upon placement of the ventilation tube 100.

Figure 14:
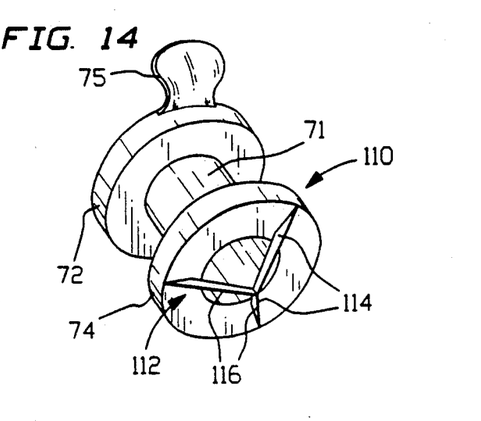

As shown in FIG. 14, a further tympanic ventilation tube device 110 also has tubular member 71, proximal flange 72, and distal flange 74. A cutting element 112 on distal flange 74 has three arms 114 connected to one another in a tripod-like configuration. Cutting edges 116 on tripod arms 114 are pointed in a distal direction. As in the embodiment of FIG. 13, the cutting element 112 of ventilation tube device 110 is spaced from the distal end of tubular member 71, facilitating access thereto by middle ear fluid.

Figure 15:
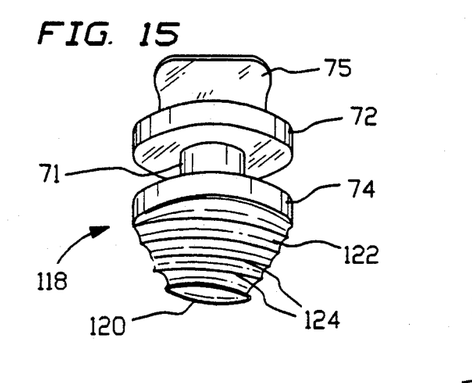

As illustrated in FIG. 15, an additional tympanic ventilation tube device 118 with tubular member 71, proximal flange 72, and distal flange 74 is formed with a generally circular or oval cutting edge 120 formed on the distal end of a screw type extension 122 on distal flange 74. Screw extension 122 has an outwardly projecting helical edge 124 which facilitates an insertion and seating of tube device 118 upon an incising of a tympanic membrane by cutting edge 120. Upon such an incising, tube 118 is rotated to move distal flange 74 through the perforated tympanic membrane and into the middle ear.

In all of the embodiments of FIGS. 9-15, the respective ventilation tube device may be inserted or placed via obturator 22 (FIG. 3) or a hollow obturator as discussed hereinafter with reference to FIG. 18. Alternatively or additionally, insertion and placement may be implemented via a grasping forceps (see FIGS. 5 and 6) which grips tongue extension 75.

Figure 16A:
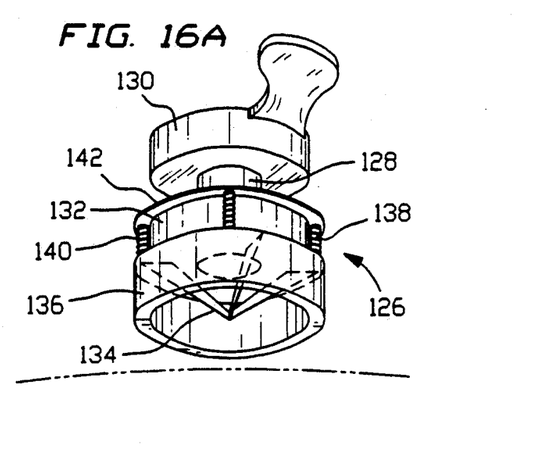
FIGS. 16A-16C are schematic perspective views, on a substantially enlarged scale, showing successive steps in the use of yet another implant or ventilation tube in accordance with the present invention.

As illustrated in FIG. 16A, another tympanic ventilation tube device 126 for releasing fluid from the middle ear comprises a tubular member 128, a first flange 130 connected to a proximal end of the tubular member, a second flange 132 connected to a distal end of the tubular member, and a tripod-type cutting element 134 connected to distal flange 132 and pointing in a distal direction therefrom. A protective collar 136 is shiftably mounted to tubular member 128 and distal flange 132 for motion in an axial direction. Collar 136 is slidably mounted to a plurality of circumferentially spaced and longitudinally or axially extending guide elements 138 an is biased to a distal protection position, shown in FIG. 16A, by a plurality of helical springs 140 surrounding guide elements 138. Guide elements 138 extend from an annular flange extension 142 projecting radially beyond the outer cylindrical surface of distal flange 132.

Figure 16B:
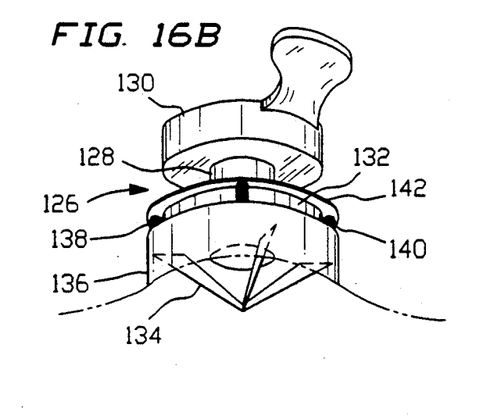
Figure 16C:
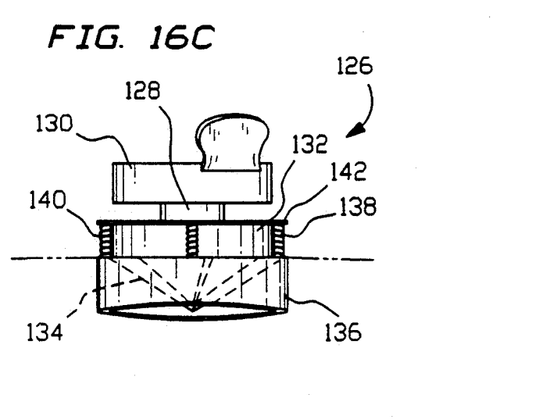

FIG. 16A shows ventilation tube device 126 spaced from a schematically illustrated tympanic membrane TMM. FIG. 16B shows tube device 126 in an intermediate stage during an incising and placement operation. As illustrated in FIG. 16B, protective collar or shield 136 is pressed against tympanic membrane TMM and, in response to the pressure exerted by the membrane, retracts in a proximal direction to expose tripod-like cutting element 134. Cutting element 134 simultaneously perforates membrane TMM until an opening is formed which is large enough to accommodate protective collar 136. At that time, collar 136 is pressed in the distal direction under the action of springs 140, as depicted in FIG. 16C. Tube device 126 is then pressed an additional distance in the distal direction so that flange 132 is moved through the perforation in tympanic membrane TMM and is seated on an inner side of the membrane, while proximal flange 130 is seated on the outer side of the membrane. Upon completion of the seating of tube 126, the tube has the configuration illustrated in FIG. 16A. Protective collar 136 is extended over cutting element 134 to shield middle ear structures from possible damage due to the cutting element.

It is to be noted that any of the ventilation tubes of FIGS. 9-15 may be provided with protective collar 136. Also, the spring loaded collar may be formed in a simpler way, for example, with a single helical spring element (not shown) surrounding the distal flange, the spring element being integral with the protective collar.

Figure 17A:
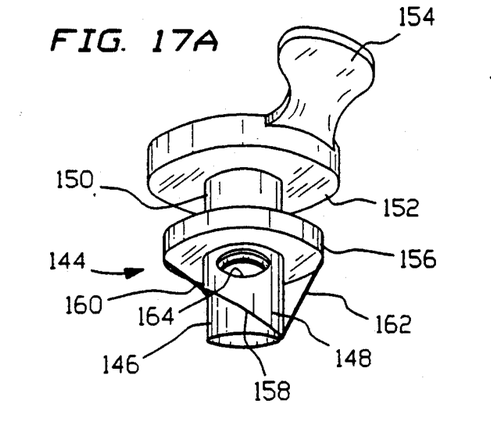
FIGS. 17A and 17B are schematic perspective views, on a substantially enlarged scale, showing different operational configurations of yet another implant or ventilation tube in accordance with the present invention.
Figure 17B:
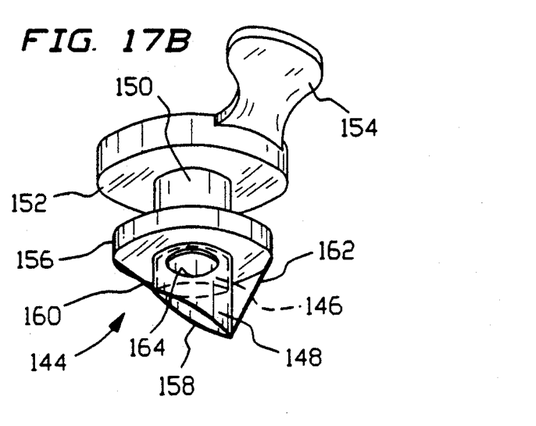

FIGS. 17A and 17B illustrate another tympanic ventilation tube device 144 with a spring loaded protective element 146 in the form of a cylinder slidably inserted inside a cylindrical axial extension 148 of a tubular member 150. Tubular member 150 connects a proximal flange 152 having a tongue 154 with a distal flange 156. At a distal end, cylindrical extension 148 is formed with a beveled cutting edge 158. A plurality of elongate cutting strips 160 and 162 extend from a distal end of cylindrical extension 148 to an outer periphery of distal flange 156. Cylindrical extension 148 is formed with one or more apertures 164 which are open and communicate with tubular member 150 in an extended, protective position of protective element 146.

FIG. 17A shows tube device 144 with protective element 146 in an extended, protective position, while FIG. 17B shows the ventilation tube device with protective element 146 in a retracted position, enabling cutting of a tympanic membrane by edge 158. Upon a pressing of tube device 144 against a tympanic membrane, element 146 retracts (FIG. 17B) and edge 158 forms a perforation in the membrane. The perforation is enlarged by cutting strips or blade elements 160 and 162, thereby enabling an insertion of distal flange 156 through the perforation and into the middle ear. Upon completion of insertion, protective element 146 shifts back into the extended position to protect inner ear structures from cutting edge 158 and strips 160 and 162.

Proximal flange 152 is wider than distal flange 156. These relative dimensions serve to facilitate insertion of the distal flange 156 and to prevent accidental insertion of proximal flange 152. Many, if not all, of the ventilation tubes disclosed herein may have a similar dimensional difference between the proximal flange and the distal flange.

Figure 18:
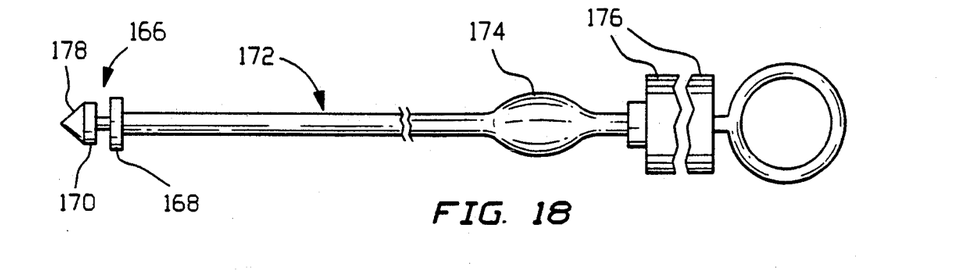
FIG. 18 is a side elevational view, on an enlarged scale, of a ventilation tube with placement obturator and syringe, for use in a method in accordance with the present invention.

As illustrated in FIG. 18, a ventilation tube 166 with a relatively wide proximal flange 168 and a relatively narrow distal flange 170 is releasably attached to the distal end of a tubular or hollow obturator 172. At a proximal end, obturator 172 is formed with a widened portion 174 to facilitate manipulation of the obturator. In addition, obturator 172 is removably connected at the proximal end to a syringe 176. Upon an incising of a tympanic membrane with a cutting element 178 on distal flange 170 and upon insertion of distal flange 170 through the membrane, syringe 176 may be operated to generate a vacuum or suction force inside obturator 172, thereby drawing fluid from the middle ear of the patient into at least the distal end of the obturator. The fluid may be ejected from obturator 172, or from syringe 176, into a vial for testing or sampling purposes.

Figure 19:
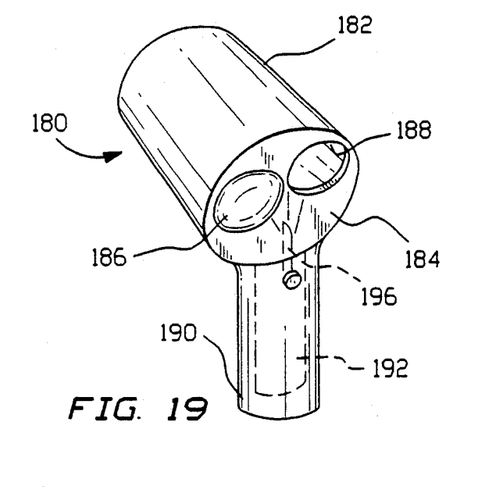
FIG. 19 is a schematic perspective view of an otoscope for use in accordance with the present invention.

As illustrated in FIG. 19, an otoscope 180 for use in performing a myringotomy comprises a conical nose portion 182 and a cover member 184 attached to the nose portion at a wider end thereof. Cover member 184 is provided with a magnifying lens 186 and an opening 188 for enabling the insertion of an instrument (e.g., obturator 22 or 172 with attached ventilation tube) into a patient's ear canal. A handle 190 is attached to nose portion 182 and cover member 184, the handle being provided with a light source 192. A prism 194 (FIG. 20), an optical fiber 196 or other optical element is provided transmitting light from source 192 to nose portion 182 and for directing light in a direction generally coaxial with the nose portion.

Figure 20:
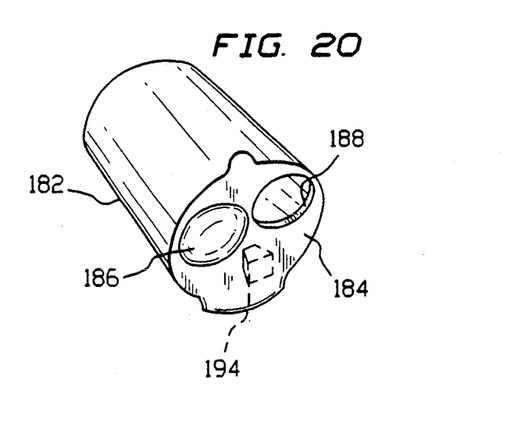
FIG. 20 is a schematic perspective view of a disposable portion of the otoscope of FIG. 19.

As indicated by FIG. 20, handle 190 is removably attachable to nose portion 182. Nose portion 182 and cover member 184 may be formed as an integral piece.

Figure 21:
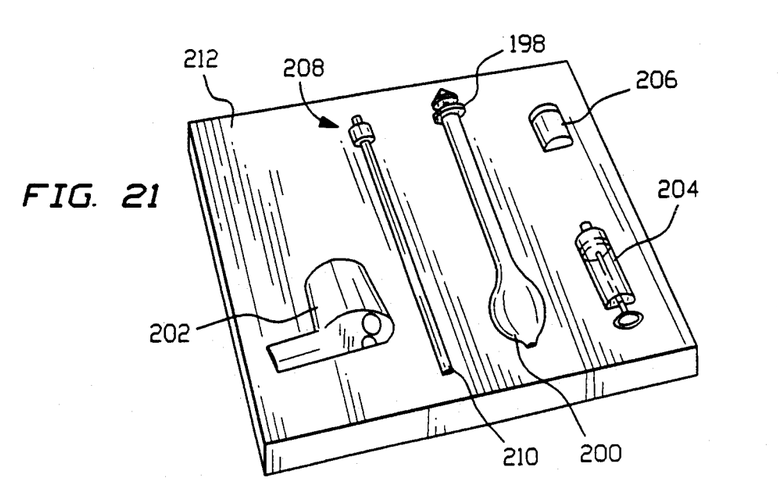
FIG. 21 is a schematic perspective view of a myringotomy kit in accordance with the present invention.

FIG. 21 illustrates a kit for use in performing a myringotomy operation. The kit includes a ventilation tube 198 provided at a distal end with a cutting edge, a placement obturator 200 releasably connected to tube 198 at a proximal end thereof, a disposable otoscope 202 (see FIG. 20), a syringe 204 connectable to a proximal end of obturator 200 for aspirating a quantity of fluid into a distal end of the obturator, a culture vial 206, and a local anesthetic applicator 208 having an elongate handle portion 210. A container 212 encloses and holds all of the operational elements of the kit.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are profferred by way of example to facilitate comprehension of the invention and should not be construed to limit the scope thereof.

What is claimed is:

1. A kit for use in performing a myringotomy operation, comprising:
    a ventilation tube provided at a distal end with a cutting edge;
    a placement obturator releasably connected to said ventilation tube at a proximal end thereof;
    a disposable otoscope:
    a syringe connectable to a proximal end of said obturator for aspirating a quantity of fluid into a distal end of said obturator;
    a culture vial;
    a local anesthetic applicator having an elongate handle portion; and
    a container enclosing said ventilation tube said placement obturator, said otoscope, said syringe, said culture vial, and said local anesthetic applicator.

2. The kit defined in claim 1 wherein said ventilation tube includes a pair of spaced flanges and wherein said cutting edge is on one of said flanges.

3. The kit defined in claim 1 wherein said obturator is hollow.

4. The kit defined in claim 1 wherein said otoscope includes:

a conical nose portion;

a cover member attached to said nose portion at a wider end thereof, said cover member being provided with a magnifying lens and an opening for enabling the insertion of an instrument through said cover member and said nose portion into a patient's ear canal;

means connected to said nose portion for removably attaching a handle to said nose portion at said wider end; and means attached to said nose portion for transmitting light from a source in the handle and for directing light in a direction generally coaxial with said nose portion.

* * * * *